(12) United States Patent
Meyer et al.

(10) Patent No.: US 7,151,174 B2
(45) Date of Patent: Dec. 19, 2006

(54) PROCESS FOR MAKING A NON-NUCLEOSIDE HIV-1 REVERSE TRANSCRIPTASE INHIBITOR

(75) Inventors: Oliver Meyer, Dorsheim (DE); Ingo Heddesheimer, Monzingen (DE); Georg Zerban, Ingelheim (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 0 days.

(21) Appl. No.: 11/264,281

(22) Filed: Nov. 1, 2005

(65) Prior Publication Data

US 2006/0100200 A1    May 11, 2006

(30) Foreign Application Priority Data

Nov. 5, 2004    (EP)    ................... 04026241

(51) Int. Cl.
*C07D 471/14*    (2006.01)
(52) U.S. Cl. .................................... 540/495
(58) Field of Classification Search ................ 540/495
See application file for complete search history.

(56) References Cited

FOREIGN PATENT DOCUMENTS

| WO | 0196338 | 12/2001 |
|---|---|---|
| WO | 2004002989 | 1/2004 |

OTHER PUBLICATIONS

Brik, M.E.; Oxidation of Secondary Amines to Nitroxides with Oxone in Aqueous Buffered Solution; Tetrahedron Letters, Elsevier, Amsterdam, NL; vol. 36, No. 31, pp. 5519-5522; Jul. 31, 1995.

*Primary Examiner*—Bruck Kifle
(74) *Attorney, Agent, or Firm*—Michael P. Morris; Mary-Ellen M. Devlin; Alan R. Stempel

(57) ABSTRACT

The invention provides a process for making compounds of the general formula I:

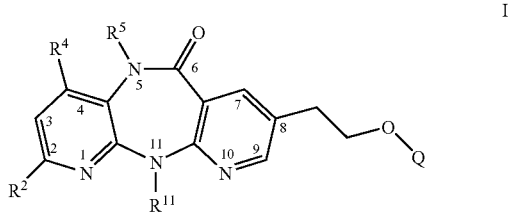

wherein $R^2$, $R^4$, $R^5$, $R^{11}$ and Q are defined as in claim 1. The compounds of the general formula I are effective inhibitors of HIV reverse transcriptase.

8 Claims, No Drawings

PROCESS FOR MAKING A NON-NUCLEOSIDE HIV-1 REVERSE TRANSCRIPTASE INHIBITOR

TECHNICAL FIELD OF THE INVENTION

The invention relates to a process for making compounds of the general formula I:

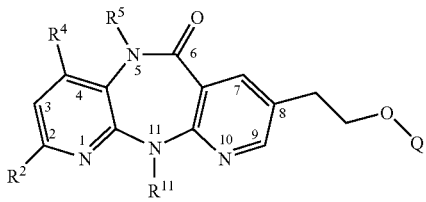

wherein $R^{11}$, $R^2$, $R^4$, $R^5$ and Q are as defined herein.

BACKGROUND OF THE INVENTION

In the WO 01/96338 A1 compounds of the general formula I

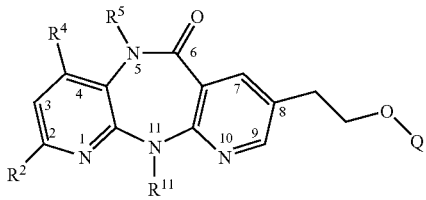

are described, wherein $R^{11}$, $R^2$, $R^4$, $R^5$ and Q are as defined therein. These compounds and their pharmaceutically acceptable salts are effective inhibitors of wild type HIV reverse transcriptase as well as inhibitors of several mutant strains. Due to their HIV-1 inhibitory activity these compounds are useful in the treatment of AIDS, ARC and related disorders associated with HIV-1 infection.

Several compounds according to the formula I wherein Q is a 1-oxido-4-quinolinyl- or 1-oxido-5-quinolinyl-group are disclosed in the WO 01/96338 A1. Their synthesis is depicted in the scheme 5 wherein a hydroxyquinoline is added to a 5,11-dihydro-8-(2-hydroxyethyl)-6H-dipyrido[3,2-b:2',3'-e][1,4]diazepin-6-one derivative in the presence of diisopropyl azodicarboxylate (DIAD) and $Ph_3P$ in THF (see example IX, step g)).

Furthermore in the WO 04/02989 a process and novel intermediates for making HIV reverse transcriptase inhibitors of the above formula I are described. The process involves the reaction of a halogene substituted 5,11-dihydro-6H-dipyrido[3,2-b:2',3'-e][1,4]diazepin-6-one with a malonate or malonate surrogate, the hydrolysis of the intermediate to yield a carboxylic acid or ester and the reduction of the carboxylic acid or ester group to yield a hydroxymethyl group. In a final step a quinolinol or oxyquinolinol is condensed.

M. E. Brik (Tetrahedron Letters Vol. 36, No. 31, 1995, pp. 5519–5522) describes the oxidation of secondary amines to nitroxides with OXONE® (trademark E.I. du Pont de Nemours) in an aqueous buffered solution. The active ingredient of OXONE® is peroxomonosulfate as annotated (see footnote 19). The phase-transfer reaction reported therein was carried out at 0° C. using a slight excess of OXONE® for the oxidative transformation. The acetone-catalyzed oxidation by peroxomonosulfate (OXONE®) was performed in $CH_2Cl_2$/buffered water (pH 7.5–8), biphasic system and $Bu_4NHSO_4$ as a phase-transfer catalyst. The process involves the formation of dimethyloxirane by nucleophilic attack of the peroxomonosulfate on the carbonyl carbon with subsequent loss of potassium hydrogen sulfate. The oxygen is transfered to the secondary amine in a biphasic medium affording the oxidized product (nitroxide) and regenerating the initial ketone. As secondary amines derivatives of 2,5-dihydropyrrole, pyrrolidine, oxazolidine, diphenylamine, 10,11-dihydro-5H-dibenzo[b,f]azepine were transformed to the respective nitroxide products.

SUMMARY OF THE INVENTION

The invention provides a process for making compounds of the general formula I:

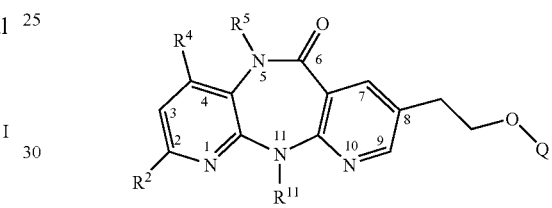

wherein
$R^2$ is selected from the group consisting of H, F, Cl, $C_{1-4}$ alkyl, $C_{3-4}$ cycloalkyl and $CF_3$;
$R^4$ is H or Me;
$R^5$ is H, Me or Et;
$R^{11}$ is Me, Et, cyclopropyl, propyl, isopropyl, or cyclobutyl;
Q is selected from the group consisting of:

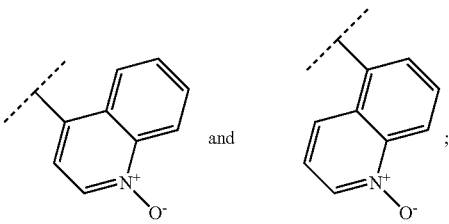

as well as pharmaceutically acceptable salts thereof,
which process comprises the step:
reacting a starting compound of the formula II

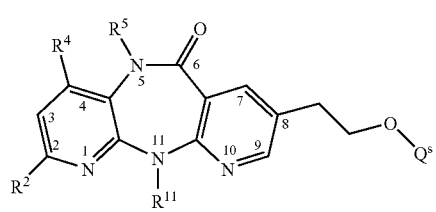

wherein $R^2$, $R^4$, $R^5$ and $R^{11}$ are as hereinbefore defined and wherein the group $Q^S$ is selected from the group consisting of:

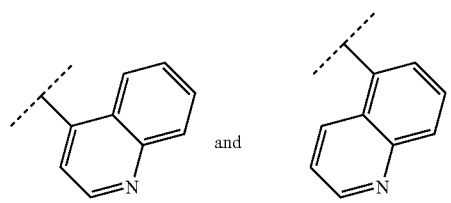

and

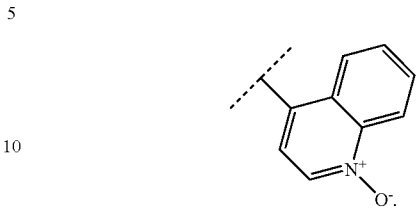

with an oxidizing agent comprising at least one reagent selected from the group consisting of peroxomonosulfuric acid, a salt of peroxomonosulfuric acid, peroxodisulfuric acid and a salt of peroxodisulfuric acid, in the presence of at least one ketone.

The inventors surprisingly found that the use of an oxidizing agent comprising at least one reagent selected from the group consisting of peroxomonosulfuric acid, a salt of peroxomonosulfuric acid, peroxodisulfuric acid and a salt of peroxodisulfuric acid, in the presence of at least one ketone selectively oxidizes the N-atom at the quinoline group. Unexpectedly the N-atoms of the 5,11-dihydro-6H-dipyrido[3,2-b:2',3'-e][1,4]diazepin-6-one scaffold are not oxidized or oxidized at a negligibly low rate.

The process of this invention allows a safe manufacture of a non-nucleoside reverse transcriptase inhibitor. Furthermore there is almost no or very little formation of unwanted byproducts formed in the inventive process. The process of this invention yields the product in a very good purity. Therefore further steps of purification may become superfluous.

Thus the process according to this invention allows a synthesis of reverse transcriptase inhibitors of the formula I in high yields, with high purity, at low technical cost and in a high space/time yield.

DETAILED DESCRIPTION OF THE INVENTION

As used herein, the term "$C_{1-4}$ alkyl" is intended to mean linear or branched alkyl radicals containing from one to four carbon atoms and includes methyl, ethyl, propyl, isopropyl, butyl, sec-butyl and tert-butyl. The terms "Me" and "Et" indicate a methyl or ethyl group respectively.

As used herein, the term "$C_{3-4}$ cycloalkyl" is intended to mean saturated cyclic hydrocarbon radicals containing three to four carbon atoms and includes cyclopropyl and cyclobutyl.

A preferred embodiment of this invention relates to a process for making compounds of the general formula I wherein $R^2$ is Cl, F, or H. More preferably, $R^2$ is Cl or H. Most preferably, $R^2$ is H.

Furthermore a preferred embodiment of this invention relates to a process for making compounds of the general formula I wherein $R^4$ is H.

A further preferred embodiment of this invention relates to a process for making compounds of the general formula I wherein $R^5$ is Me.

In the process according to this invention compounds of the general formula I are preferred wherein $R^{11}$ is Et or cyclopropyl. More preferably, $R^{11}$ is Et.

Furthermore a preferred embodiment of this invention relates to a process for making compounds of the general formula I wherein Q is

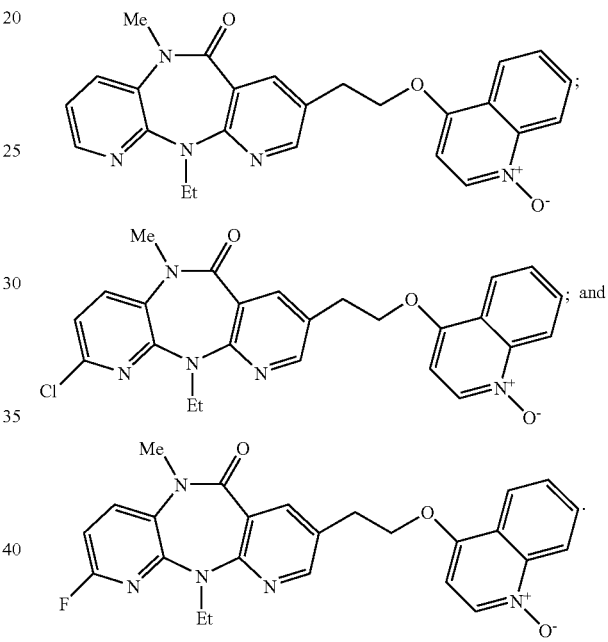

Particularly preferred embodiments of this invention relate to a process for making compounds selected from the group consisting of:

In the process according to this invention the oxidizing agent comprises at least one reagent selected from the group consisting of peroxomonosulfuric acid, a salt of peroxomonosulfuric acid, peroxodisulfuric acid and a salt of peroxodisulfuric acid.

Peroxomonosulfuric acid is also known as Caro's acid and can be depicted as HO—$SO_2$—O—OH($H_2SO_5$).

Salts of peroxomonosulfuric acid are known, in particular alkali peroxomonosulfates, ammonium peroxomonosulfate, tetraalkylammonium peroxomonosulfates and phosphonium peroxomonosulfates. Examples of the alkali salts are potassium hydrogenperoxomonosulfate ($KHSO_5$ and $KHSO_5 \times H_2O$), potassium monopersulfate and the stable triple salt 2 $KHSO_5 \times KHSO_4 \times K_2SO_4$. Examples of tetraalkylammonium salts are tetra-n-butylammonium peroxomonosulfate, tetra-n-pentylammonium peroxomonosulfate and tetra-n-hexylammonium peroxomonosulfate. Examples of phosphonium salts are aryl-/arylalkyl-phosphonium peroxomonosulfates such as benzyltriphenylphosphonium peroxomonosulfate.

Peroxodisulfuric acid can be depicted as HO$_3$S—O—O—SO$_3$H (H$_2$S$_2$O$_8$).

Salts of peroxodisulfuric acid are also known as persulfates. Examples thereof are ammonium persulfate, sodium peroxodisulfate and potassium peroxodisulfate.

Furthermore tetraalkylammonium peroxodisulfates are known, for example bis(tetrabutylammonium) peroxodisulfate. Sodium persulfate copper sulphate is also known as an ingredient of Kjeldahl tabletts.

According to this invention an oxidizing agent comprising at least one salt of peroxomonosulfuric acid is preferred. In particular the alkali salts and the tetraalkylammonium salts are preferred, wherein alkyl is a C$_{1-8}$ alkyl group, preferably a C$_{1-6}$ alkyl group, most preferably a straight chain C$_{4-6}$ alkyl group, and wherein alkali is preferably sodium or potassium.

An especially preferred alkali hydrogenperoxomonosulfate is potassium hydrogenperoxomonosulfate. Potassium hydrogenperoxomonosulfate is commonly known as potassium monopersulfate or as potassium peroxymonosulfate.

An especially preferred tetraalkylammonium hydrogenperoxomonosulfate is tetra-n-butylammonium peroxomonosulfate.

Most preferably the oxidizing agent comprises potassium hydrogenperoxomonosulfate, for example as a component of a triple salt. Such a triple salt can be represented by the formula 2 KHSO$_5$×KHSO$_4$×K$_2$SO$_4$ and is known as Caro's salt.

Triple salts of the formula 2 KHSO$_5$×KHSO$_4$×K$_2$SO$_4$ are commercially available, for example under the brand names OXONE® (trademark E.I. du Pont de Nemours) and CAROAT® (trademark Degussa, Peroxid-Chemie GmbH & Co. KG, Dr.-Gustav-Adolph-Str. 3, D-82049 Pullach, Germany).

The synthesis of tetraalkylammonium peroxomonosulfates is known to the skilled one in the art (for example: B. R. Travis et al., Eur. J. Org. Chem. 2002, 3429–3434).

In general 2 moles of a peroxomonosulfate (as a salt, in particular as hydrogenperoxomonosulfate, or as a free acid) are theoretically needed to oxidize 1 mole of the N-containing compound to yield the respective N-oxido derivative.

Therefore a preferred amount of the oxidizing agent is such that it corresponds to at least 2 moles of hydrogenperoxomonosulfate per 1 mole of the starting material of formula II. In case a triple salt of the above given formula is used, which contains 2 moles hydrogenperoxomonosulfate per mole of the triple salt, the preferred amount corresponds to at least 1 mole per 1 mole of starting material of formula II.

More preferably the amount of the oxidizing agent is such that it corresponds to a range from 2 to 6 moles of hydrogenperoxomonosulfate, particularly from 2 to 4 moles, most preferably from 2.1 to 3 moles per 1 mole of the starting material of formula II.

In case a triple salt of the above given formula is used, the preferred amount of the oxidizing agent corresponds to a range from 1 to 3 moles, particularly from 1 to 2 moles, most preferably from 1.05 to 1.5 moles per 1 mole of the starting material of the formula II.

The process according to this invention uses the oxidizing agent in the presence of at least one ketone. Preferred ketones are C$_{3-8}$-alkanones, C$_{5-7}$-cyloalkanones or 1-phenyl-C$_{2-4}$-alkanones, wherein C-atoms of the cycloalkanone, the alkanone or the alkanone group of the phenyl-alkanone are unsubstituted or substituted with one or more fluorine atoms, and wherein the phenyl group is unsubstituted or substituted with one or more substituents. Preferred substituents of the phenyl group are independently of each other selected from group consisting of F, Cl, Br, hydroxy, cyano, C$_{1-3}$-alkyl and C$_{1-3}$-alkoxy, wherein said alkyl or alkoxy group may be substituted with 1 or more fluorine substituents.

Most preferred ketones are acetone, methyl ethyl ketone, diethyl ketone, cyclohexanone, cyclopentanone, acetophenone, propiophenone, butyrophenone, phenylacetone (1-phenyl-2-propanone), 4-phenyl-2-butanone or mixtures thereof, in particular acetone.

The above mentioned ketone putatively serves as a catalyst. The ketone in its function as a catalyst is most likely transformed to the corresponding dioxirane (for example dimethyldioxirane in the case of acetone) that subsequently transfers an oxygene to form the N-oxide and is finally regenerated. Therefore the amount of the ketone to be used is principally not essential to the process of this invention. However in order not to be for example limiting the reaction rate it is advantageous to use the ketone in a stoichiometric excess compared with the starting material of the formula II. Beyond its function as a catalyst the ketone may serve as a solvent in the reaction mixture.

According to a first embodiment the process of this invention may be carried out in a solvent or a mixture of solvents which exhibits sufficient solubility properties in view of the starting material of the formula II and the oxidizing agent. A mixture of water and at least one organic solvent which is sufficiently soluble in water is preferred. Preferred organic solvents with such properties are alcohols and ketones. Examples of preferred organic solvents are methanol, ethanol, acetone, methyl ethyl ketone, diethyl ketone, cyclohexanone and cyclopentanone. According to this embodiment the process is most preferably carried out in an acetone/water mixture.

According to a second embodiment the process of this invention is carried out in a reaction mixture comprising two liquid phases, preferably under phase-transfer conditions. Advantageously a biphasic solvent system and one or more phase-transfer catalysts are used. Preferred solvents of the first phase are aprotic organic solvents, in particular benzene, toluene, xylenes, alkanes (for example pentane, hexane, heptane, octane), dimethylacetamide, acetonitrile, halogenated alkanes (for example CH$_3$Cl, CH$_2$Cl$_2$, CHCl$_3$, CCl$_4$) and mixtures thereof. A particularly preferred solvent of the first phase comprises a chlorinated C$_{1-3}$-alkane which additionally may have one or more fluorine substituents, most preferably CH$_2$Cl$_2$.

The second phase is preferably an aqueous mixture of solvents. Preferably the second phase comprises water and at least one solvent selected from alkanols and ketones. Particularly preferred solvents are selected from methanol, ethanol, n-propanol, i-propanol, acetone, methyl ethyl ketone, diethyl ketone, cyclohexanone and cyclopentanone and mixtures thereof; most preferably methanol and/or ethanol. A preferred second phase is based on a methanol/water or ethanol/water mixture or a mixture of methanol and ethanol with water, wherein a preferred volume ratio of the alcohol to water is from 1:1 to 1:10.

A preferred ratio of the volume of the first solvent phase to the volume of the second (aqueous) phase is in the range from 1:1 to 1:20.

Preferred phase-transfer catalysts possess a quarternary ammonium cation, as for example tetraalkylammonium compounds, such as tetramethylammonium compounds, tetraethylammonium compounds or tetrabutylammonium compounds. Most preferred phase-transfer catalyst are tetrabutylammonium compounds, in particular tetrabutylammonium salts with inorganic acids, such as tetrabutylammonium chloride, tetrabutylammonium bromide, tetrabutylammonium hydrogensulfate, etc.

The preferred amount of the phase-transfer catalyst depends on the kind of solvents used and their quantities and can be determined by standard experimentation. Usually per 1 mole of the starting material of the formula II an amount from 0.01 to 0.5 mole of a phase-transfer catalyst is used.

Advantageously the aqueous solvent phase is basified or buffered. During and after the addition of the oxidizing agent, preferred pH-values of the aqueous solvent phase are greater than or equal to about 7, in particular in the range from about 7 to about 13, more preferably in the range from about 8 to about 12, most preferably in the range from about 10 to about 11.

The pH value is kept in the desired basic pH range advantageously by the addition of at least one basifying reagent, preferably selected from the group consisting of hydroxides, hydrogencarbonates, carbonates, phosphates and/or borates. The corresponding alkali salts are preferred, as for example sodium carbonate, sodium hydrogencarbonate, sodium hydroxide, potassium carbonate, potassium hydrogenphosphate, potassium hydroxide and/or sodium borate. Advantageously the basifying reagent is added in the form of an aqueous solution.

Preferably the pH value is kept in the desired basic pH range by using a buffer system to make the pH-adjustment easier. One or more buffer reagents are preferably selected from the group consisting of hydrogencarbonates, carbonates, phosphates and/or borates. The corresponding alkali salts are preferred, as for example sodium carbonate, sodium hydrogencarbonate, potassium carbonate, potassium hydrogenphosphate, and/or sodium borate. Advantageously the buffer reagent is used in the form of an aqueous solution. A basifying reagent, for example a hydroxide, may be used in addition to a buffer system.

Advantageously the oxidizing agent is added continuously (e.g. dropwise) to the solvent system comprising the starting material of the formula II over a given period of time, for example 20 min to 24 hours, preferably 40 min to 10 hours. After the addition of the oxidizing agent the reaction mixture is advantageously stirred for another period of time, preferably from 20 min to 24 hours.

A preferred temperature range of the reaction mixture during and after the addition of the oxidizing agent is in the range from about −10° C. to about 40° C., more preferably in the range from about −1° C. to about 30° C., most preferably in the range from about 10° C. to about 25° C.

The process according to this invention is preferably carried out at normal atmospheric pressure. As the process is not sensitive to the pressure, it can be carried out at slightly reduced pressure or at an elevated pressure also.

Preferably the process according to this invention is carried out in the absence of light or in dim light conditions due to a possible light sensitivity of the product.

Advantageously any excess of the oxidizing agent is eliminated before the product is isolated. Suitable reagents for a degradation of the oxidizing agent are known to the skilled one in the art. Examples are thiosulfates, sulfites or dithionites, in particular sodium thiosulfate. The one or more reagents are added to the reaction mixture until peroxides can not be detected any more. Advantageously the temperature of the reaction mixture is kept at an elevated temperature from about 10 to about 40° C. during and/or after the addition of the reagent.

The product of the formula I can be isolated from the reaction mixture and purified by methods very well known to persons skilled in the art. For example the product can be obtained by filtering the reaction mixture and washing the raw solid product with water and/or a water soluble solvent or mixture thereof. The product can be converted to a salt, especially a pharmaceutically acceptable salt, if wanted.

The starting material according to the formula II can be obtained by methods as described for example in WO 01/96338 or WO 04/02989.

The following examples shall illustrate the invention without limiting the invention in its scope.

EXAMPLES

All examples refer to the following reaction scheme:

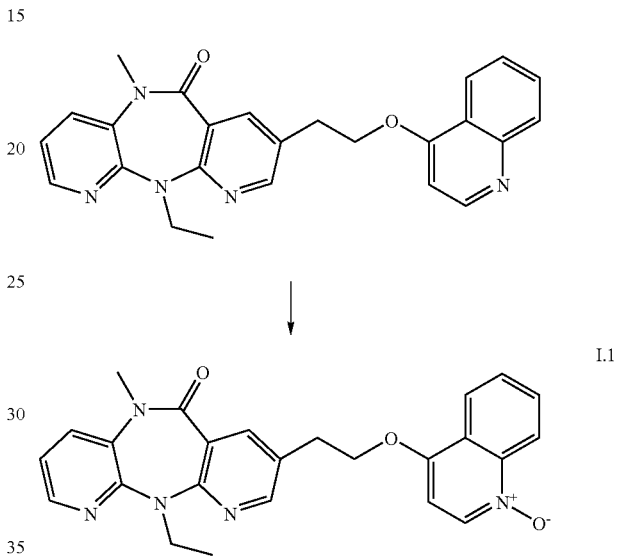

The synthesis of the starting material according to the formula II.1 is described in the WO 01/96338 and WO 04/02989.

Example 1

A flask is charged with 30 g of the compound II.1, 1.41 g tetrabutylammonium hydrogensulfate, 75 ml $CH_2Cl_2$ and 105 ml methanol. The mixture is stirred until the compounds are dissolved and then 75 ml acetone and a solution consisting of 3.74 g sodium carbonate in 45 ml water are added. The resulting solution has a pH of approximately 11.4. A solution consisting of 56.38 g of OXONE® (2 $KHSO_5 \times KHSO_4 \times K_2SO_4$) in 228 ml water is added dropwise. During the addition of said OXONE® solution the pH of the reaction mixture is kept in a range of about 10 to 11 by adding about 24 ml of an aqueous 8 mol/l sodium hydroxide solution. The resulting suspension is continuously stirred for about an hour. After the completion of the reaction a solution consisting of about 28 g sodiumthiosulfate in 42 ml water is added, the reaction mixture is heated to about 32° C. and stirred for about an additional hour. A peroxide test kit is used to show that there are no remaining peroxides in the reaction mixture. The suspension is cooled to about 19° C. and stirred for further 30 min. Finally the suspension is filtered and the remaining solid is washed with 225 ml of water and 120 ml of acetone. The wet product is dried at 50° C. under vacuum. 34.6 g of a solid is yielded. Via HPLC a purity of about 99.3% is calculated. The main steps are performed under dim light conditions or even in the absence of light.

Example 2

A flask is charged with 2 g (4.7 mmol) of the compound II.1, 0.09 g tetrabutylammonium hydrogensulfate, 3 ml $CH_2Cl_2$, 7 ml methanol and 5 ml acetone.

A solution of 0.47 g potassium hydrogencarbonte in 6 ml water is added. The resulting solution has a pH of approximately 9.7. A solution consisting of 4.33 g of OXONE® (2 $KHSO_5 \times KHSO_4 \times K_2SO_4$) in 17 ml water is added dropwise. During the addition of said OXONE® solution the pH of the reaction mixture is kept in a range of about 8 to 9 by adding an aqueous 4 mol/l potassium hydroxide solution and the temperature is kept in a range between 20° C. and 26° C. The resulting suspension is continuously stirred for about 18 hours at a temperature of about 20° C. Finally a solution consisting of about 3.5 g sodium thiosulfate in 18 ml water is added, the reaction mixture is heated to about 30° C. and stirred for about an additional hour. A peroxide test kit is used to show that there are no remaining peroxides in the reaction mixture. To the reaction suspension an aqueous $H_2SO_4$ solution (18%) is added in an amount to obtain a pH of about 2. The suspension is cooled to about 20° C. Finally the suspension is filtered and the remaining solid is washed with 20 ml of an aqueous $H_2SO_4$ solution of a pH of about 2 and then washed with 10 ml of water. The wet product is dried at 50° C. under vacuum. 2.26 g of a solid is yielded. Via HPLC a purity of about 97% is calculated. The main steps are performed under dim light conditions or even in the absence of light.

Example 3

As the hydrochloride of the starting material of the formula II.1 is used, in the first step the neutral (non-salt) form of the compound II.1 is obtained. A flask is charged with 1.85 g (4 mmol) of the compound II.1 in the form of its hydrochloride, with 60 ml water and 50 ml $CH_2Cl_2$. Using a NaOH solution a pH of 9.7 is obtained, the phases are mixed vigorously and the phases are separated. The aqueous phase is washed with 10 ml $CH_2Cl_2$ and the organic phases are combined. To this organic solution a 80 ml acetone, 0.08 g tetrabutylammonium hydrogensulfate and an aqueous solution of 1.07 g disodium hydrogenphosphate in 60 ml water are added. The resulting emulsion is cooled to about 1° C. and basified to a pH of 8.7 by adding sodium hydroxide. The mixture is stirred and a solution consisting of 2.5 g of OXONE® (2 $KHSO_5 \times KHSO_4 \times K_2SO_4$) in 90 ml water is added slowly over a time period of about an hour. The reaction mixture is kept at about −1° C. to about 2° C. During the addition of said OXONE® solution the pH of the reaction mixture is kept in a range of about 8 to 9.5 by adding an aqueous sodium hydroxide solution. The resulting suspension is continuously stirred for about two hours. As via HPLC remaining starting material can be found, additional 0.25 g OXONE® are added and the reaction mixture is stirred for a further hour at a temperature of about 0° C. After the completion of the reaction a solution consisting of about 1 g sodium thiosulfate in 50 ml water is added twice. After about 2 hours the reaction mixture is heated to about 20° C. and stirred for about an additional hour. Finally the suspension is filtered and the remaining solid is washed with 50 ml of water. The wet product is dried at 30° C. under vacuum. 2.6 g of a solid is yielded. The main steps are performed under dim light conditions or even in the absence of light.

Example 4

As the hydrochloride of the starting material of the formula II.1 is used, in the first step the neutral (non-salt) form of the compound II.1 is obtained. A flask is charged with 1.85 g (4 mmol) of the compound II.1 in the form of its hydrochloride, with 20 ml water and 20 ml $CH_2Cl_2$. Using an aqueous NaOH solution a pH of 8.5 is obtained, the phases are mixed vigorously and then the phases are separated. The organic phase is destilled to yield an oil as a residue. To this residue 20 ml dimethylacetamide, 60 ml acetone and 0.08 g tetrabutylammonium hydrogensulfate are added. At a temperature of about 20° C. a solution of 3.69 g OXONE® (2 $KHSO_5 \times KHSO_4 \times K_2SO_4$) in 15 ml water is added dropwise. During the addition of OXONE® 10 ml water are added and using a 2 mole/l aqueous NaOH solution the pH is kept in the range from 8 to 9. The reaction mixture is stirred for about 6 hours. For a conversion of remaining starting material a solution of 1.23 g OXONE® in 5 ml water is added dropwise and the reaction mixture is stirred over night (for another 16 hours). The reaction suspension is poured into 60 ml of water and stirred for several minutes and finally filtered. The solid is dried at 40° C. in vacuum. 3.91 g are yielded.

Example 5

A flask is charged with 12.8 g (28 mmol) of the compound II.1 in the form of its hydrochloride, with 200 ml acetone and 160 ml of a phosphate buffer solution (pH 7.2; prepared from potassium dihydrogenphosphate and sodium hydroxide; commercially available from Aldrich). At a temperature of about 20° C. a solution of 51.6 g OXONE® (2 $KHSO_5 \times KHSO_4 \times K_2SO_4$) in 240 ml water is added slowly at a temperature of about 20° C. During the addition of OXONE® an aqueous 2 mole/l NaOH solution is added in order to keep the pH in the range from about 7 to 8. The total amount of the NaOH solution is about 120 ml. The reaction mixture is stirred over night. The reaction suspension is filtered and the solid is washed with 80 ml of water. The solid is dried at 65° C. in vacuum.

In the examples, the structure of the product of the formula I.1 is confirmed by NMR and HPLC-MS.

What is claimed is:

1. A process for making a compound of the formula I:

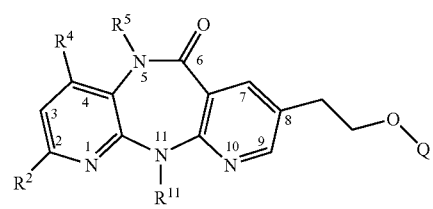

I wherein $R^2$ is selected from the group consisting of H, F, Cl, $C_{1-4}$ alkyl, $C_{3-4}$ cycloalkyl and $CF_3$;

$R^4$ is H or Me;

$R^5$ is H, Me or Et;

$R^{11}$ is Me, Et, cyclopropyl, propyl, isopropyl, or cyclobutyl;

Q is selected from the group consisting of:

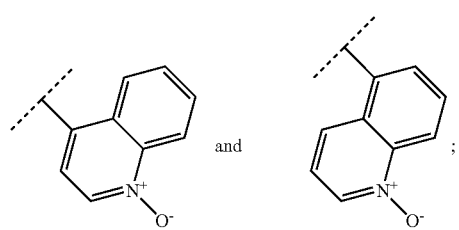

and

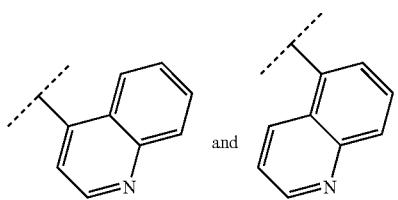

or a pharmaceutically acceptable salt thereof, which process comprises the step:

reacting a starting compound of the formula II

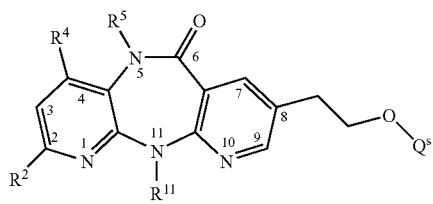

II wherein $R^2$, $R^4$, $R^5$ and $R^{11}$ are as hereinbefore defined and wherein the group $Q^S$ is selected from the group consisting of:

with an oxidizing agent comprising at least one reagent selected from the group consisting of peroxomonosulfuric acid, a salt of peroxomonosulfuric acid, peroxodisulfuric acid and a salt of peroxodisulfuric acid, in the presence of at least one ketone.

2. The process according to claim 1 wherein the oxidizing agent comprises at least one salt of peroxomonosulfuric acid.

3. The process according to claim 2 wherein the oxidizing agent is a hydrogen peroxomonosulfate.

4. The process according to claim 2 wherein the oxidizing agent is the triple salt represented by the formula 2 $KHSO_5 \times KHSO_4 \times K_2SO_4$.

5. The process according to claim 1 wherein the at least one ketone is selected from the group consisting of $C_{3-8}$-alkanones, $C_{5-7}$-cyloalkanones or 1-phenyl-$C_{2-4}$-alkanones, wherein C-atoms of the cycloalkanone, the alkanone or the alkanone group of the phenyl-alkanone are unsubstituted or substituted with one or more fluorine atoms, and wherein the phenyl group is unsubstituted or substituted with one or more substituents.

6. The process according to claim 1 wherein the at least one ketone is acetone.

7. The process according to claim 1 wherein the process is carried out in a reaction mixture comprising an aqueous solvent phase whereby the pH-value of the aqueous solvent phase is greater than or equal to about 7.

8. The process according claim 1 wherein the process is carried out under phase-transfer conditions in a reaction mixture comprising two liquid phases.

\* \* \* \* \*